(12) United States Patent
Lin (10) Patent No.: US 11,207,359 B2
(45) Date of Patent: Dec. 28, 2021

(54) CHOLESTEROL REDUCING PROBIOTIC STRAIN AND USE THEREOF

(71) Applicant: TCI CO., LTD., Taipei (TW)

(72) Inventor: Yung-Hsiang Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 140 days.

(21) Appl. No.: 16/530,557

(22) Filed: Aug. 2, 2019

(65) Prior Publication Data

US 2020/0254032 A1     Aug. 13, 2020

(30) Foreign Application Priority Data

Feb. 12, 2019   (TW) ................................ 108104652

(51) Int. Cl.
| | | |
|---|---|---|
| *A61K 35/747* | (2015.01) | |
| *A61P 9/00* | (2006.01) | |
| *A23L 2/38* | (2021.01) | |
| *A23L 33/135* | (2016.01) | |
| *A61K 9/00* | (2006.01) | |

(52) U.S. Cl.
CPC .............. *A61K 35/747* (2013.01); *A23L 2/38* (2013.01); *A23L 33/135* (2016.08); *A61K 9/0053* (2013.01); *A61P 9/00* (2018.01)

(58) Field of Classification Search
CPC ... A61K 35/747; A61K 2035/115; A61P 9/00; A23L 33/135; A23V 2002/00; A23Y 2220/67
See application file for complete search history.

(56) References Cited

U.S. PATENT DOCUMENTS

2012/0213753 A1* 8/2012 Cune Castellana .... A61K 35/74
424/93.45

* cited by examiner

*Primary Examiner* — Lynn Y Fan
(74) *Attorney, Agent, or Firm* — Chieh-Mei Wang (57) ABSTRACT

The present invention provides a cholesterol reducing probiotic strain, composition thereof and use thereof. The probiotic strain is *Lactobacillus plantarum* TCI507, which itself and its metabolites can effectively reduce the cholesterol content, enhance the gene expression level of SCARB1, APOA1, and LDLR to promote the effect of cholesterol metabolism, and can effectively reduce the total cholesterol and the low-density lipoprotein in human blood.

8 Claims, 4 Drawing Sheets

Specification includes a Sequence Listing.

CHOLESTEROL REDUCING PROBIOTIC STRAIN AND USE THEREOF

CROSS-REFERENCE TO RELATED APPLICATION

This application claims priority of Taiwan application No. 108104652, filed on Feb. 12, 2019 the content of which is incorporated herein in its entirety by reference.

BACKGROUND OF THE INVENTION

1. Field of the Invention

The present invention relates to a cholesterol reducing probiotic strain, composition thereof and use thereof, and more particularly to the *Lactobacillus plantarum* TCI507 and the metabolite thereof for enhancing the gene expression level of SCARB1, APOA1, or LDLR, and reducing the level of total cholesterol or low-density lipoprotein (LDL) in the blood.

2. The Prior Art

According to relevant statistics, about one-third of population in the world die from cardiovascular disease (CVD), ranking first in the global cause of death. Cardiovascular disease is also called circulatory disease which is developed in organs and tissues that transport blood in bodies, so all heart and blood vessel diseases can be called cardiovascular diseases, such as stroke, myocardial infarction and the like. Wherein, hypercholesterolemia has a prevalence rate of 70% in patients with cardiovascular disease and is also a major risk factor for atherosclerosis such as coronary artery disease, stroke, and peripheral vascular disease.

However, hypercholesterolemia mostly has no obvious symptoms, only atypical symptoms such as dizziness, neck stiffness and elevated blood pressure. When the degree of vascular occlusion becomes more and more serious, serious complications such as angina, myocardial infarction, stroke, or intermittent claudication would occur. Therefore, in order to reduce the risk of cardiovascular disease, controlling blood cholesterol levels has become a primary goal.

Wherein, current prevention of cardiovascular disease can only improve by keeping a regular lifestyle, diet, and exercise habits, and avoiding risk factors such as cigarettes. Otherwise, it must be controlled by drugs, which are mainly obtained by chemical synthesis, and can be divided into two categories: one is to prevent thrombosis or anti-platelet aggregation, and the other is to control high blood pressure, cholesterol, or diabetes; however, these two classes of drugs are often accompanied by strong side effects. For example, angiotensin-related antagonists could cause hyperkalemia, muscle weakness, or slow heartbeat, and Statins, a potent cholesterol-lowering drug, could increase liver function index, cause headaches or nausea. These kinds of drugs must be taken for a long time to control the disease, but the side effects caused by the long-term uses of the drugs cannot improve the health of the individual.

In summary, in view of the high incidence of cardiovascular disease, and based on the improvement of living standards and the health awareness of modern people living, research and development of a composition containing active ingredients from natural plants for effectively preventing cardiovascular disease, controlling the amount of cholesterol in blood, and avoiding side effects of a synthetic drug on bodies are necessary.

SUMMARY OF THE INVENTION

To solve the foregoing problem, one objective of the present invention is to provide a method of reducing cholesterol, comprising administering a composition comprising an effective amount of *Lactobacillus plantarum* TCI507 or a metabolite thereof to a subject in need thereof.

The other objective of the present invention is to provide a cholesterol reducing composition, comprising an effective amount of a *Lactobacillus plantarum* TCI507 or a metabolite thereof.

In one embodiment of the present invention, the *Lactobacillus plantarum* TCI507 is a live or deactivated bacterium.

In one embodiment of the present invention, the concentration of the *Lactobacillus plantarum* TCI507 or the metabolite in the composition is at least 0.5% (w/w), and the effective amount of the *Lactobacillus plantarum* TCI507 is $5 \times 10^9$ CFUs/individual per day.

In one embodiment of the present invention, the *Lactobacillus plantarum* TCI507 or the metabolite thereof enhance the gene expression level of Scavenger receptor class B member 1 (SCARB1), Apolipoprotein A1 (APOA1), or Low-density lipoprotein receptor (LDLR).

In one embodiment of the present invention, the *Lactobacillus plantarum* TCI507 or the metabolite thereof reduce the level of total cholesterol or low-density lipoprotein (LDL) in the blood.

The live bacterium, the deactivated bacterium or the metabolite of the *Lactobacillus plantarum* TCI507 of the present invention can effectively reduce the amount of the cholesterol in vitro showing that they have the potential of lowering cholesterol in bodies; and in cell experiments, the *Lactobacillus plantarum* TCI507 or the metabolite thereof can effectively increase the gene expression level of SCARB1, APOA1, and LDLR, indicating that they can promote the metabolism of cholesterol in bodies; and in vivo, the *Lactobacillus plantarum* TCI507 or the metabolite thereof can further effectively reduce the amount of the total cholesterol and the low-density lipoprotein in blood, showing that they can be used for lowering cholesterol in bodies; and the high cholesterol in blood would cause cardiovascular diseases such as hypertension, arteriosclerosis and myocardial infarction, so the *Lactobacillus plantarum* TCI507 or the metabolite thereof of the present invention can be used for cardiovascular healthcare. Therefore, the *Lactobacillus plantarum* TCI507 or the metabolite thereof of the present invention can be used for the preparation of a cardiovascular healthcare composition for reducing cholesterol, which is a food, a drink, a nutritional supplement, or a pharmaceutical product, and the composition is in a form of a powder, a granule, a solution, a gel can be administered to a subject in need by oral administration or the like.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

The *Lactobacillus plantarum* TCI507 of the present invention is a probiotic bacteria that can reduce the cholesterol to promote cardiovascular healthcare. The present invention is a novel *Lactobacillus plantarum* strain, which is named TCI507 in the specification, was registered in the Food Industry Research and Development Institute (Taiwan) on Dec. 21, 2017, and the number is BCRC910806. The *Lactobacillus plantarum* TCI507 was also deposited at the Leibniz Institute DSMZ (Address: Inhoffenstr. 7 B D-38124 Braunschweig), Germany, in accordance with the Budapest Treaty, on May 24, 2019, under the registration number DSM 33162. Viability test of the bacterial strain was performed and confirmed on Jun. 19, 2019. The *Lactobacillus plantarum* TCI507 or the metabolite thereof of the present invention can effectively reduce the amount of the cholesterol in vitro; and in cell experiments, the *Lactobacillus plantarum* TCI507 or the metabolite thereof can effectively increase the gene expression level of SCARB1, APOA1, and LDLR to promote the metabolism of cholesterol in bodies; and in vivo, the *Lactobacillus plantarum* TCI507 or the metabolite thereof can effectively reduce the amount of the total cholesterol and the low-density lipoprotein in blood, showing that the *Lactobacillus plantarum* TCI507 or the metabolite thereof of the present invention can be used for the preparation of a cardiovascular healthcare composition for reducing cholesterol, which is a food, a drink, a nutritional supplement, or a pharmaceutical product, and the composition is in a form of a powder, a granule, a solution, a gel can be administered to a subject in need by oral administration or the like.

Statistical analysis is performed using Excel software. Data are expressed as mean± standard deviation (SD), and the differences between these are analyzed by Student's t-test.

Definition

The data provided in the present invention represent approximated, experimental values that may vary within a range of ±20%, preferably ±10%, and most preferably ±5%.

The "probiotic", "probiotic strain", or "probiotic bacteria" describes herein is a microorganism the cells thereof, the mixed strains, the extracts or the metabolites with a positive effect on the host itself, usually derived from the human body and beneficial to intestinal health. Probiotic or probiotic bacteria can also refer to certain microorganisms that are externally supplemented and are beneficial to the body.

According to the present invention, the operating procedures and parameter conditions for bacterial culture are within the professional literacy and routine techniques of those having ordinary skill in the art.

The "metabolite" describes herein is a substance which is secreted into the bacterial culture solution after being metabolized by the bacteria, comprising the culture medium for culturing the bacteria.

According to the present invention, a pharmaceutical product can be manufactured into a form suitable for parenterally or topically administration using techniques well known to those having ordinary skill in the art, including, but not limited to, injection (for example, sterile aqueous solution or dispersion), sterile powder, external preparation, and the like.

According to the present invention, the pharmaceutical product could further comprise a pharmaceutically acceptable carrier that is widely used in pharmaceutical manufacturing techniques. For example, the pharmaceutically acceptable carrier can comprise one or more agents selected from the group consisting of a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, and the like. The selection and quantity of these reagents falls within the professional literacy and routine skills of those having ordinary skill in the art.

According to the present invention, the pharmaceutically acceptable carrier comprises a solvent selected from the group consisting of water, normal saline, phosphate buffered saline (PBS), aqueous solution containing alcohol, and combinations thereof.

According to the present invention, the pharmaceutical product can be administered by a parenteral route selected from the group consisting of subcutaneous injection, intraepidermal injection, intradermal injection and intralesional injection.

According to the present invention, the food product can be used as a food additive, added by the conventional method in the preparation of the raw material, or added during the production of the food, and matched with any edible material to be made into food products for human and non-human animals.

According to the present invention, the types of the food products include, but are not limited to, beverages, fermented foods, bakery products, health foods, and dietary supplements.

The present invention provides a method of reducing cholesterol, comprising administering to a subject in need thereof a composition composted of an effective amount of the *Lactobacillus plantarum* TCI507 or the metabolite thereof, wherein the metabolites of the *Lactobacillus plantarum* TCI507 of the present invention is obtained by taking the culture solution of the *Lactobacillus plantarum* TCI507. The *Lactobacillus plantarum* TCI507 or the metabolite thereof can increase the gene expression level of SCARB1, APOA1, or LDLR to promote metabolism of cholesterol, and can also reduce the amount of the total cholesterol or the low-density lipoprotein in bloodies.

Meanwhile, the composition for reducing cholesterol of the present invention could further comprise an effective amount of the *Lactobacillus plantarum* TCI507 or the metabolite thereof, and a pharmaceutically acceptable carrier, and the composition is a pharmaceutical product, or a food.

The test of the *Lactobacillus plantarum* TCI507 or the metabolite thereof of the present invention for reducing the amount of the cholesterol in vitro, for increasing the gene expression level of SCARB1, APOA1, and LDLR in liver cells, and for reducing the amount of the total cholesterol and the low-density lipoprotein in blood of the bodies will all be described in detail below to confirm that the *Lactobacillus plantarum* TCI507 or the metabolite thereof of the present invention can effectively promote the metabolism of cholesterol and reduce the cholesterol of the bodies, and can be used for preparing a composition for reducing cholesterol.

Example 1

Effect of the *Lactobacillus plantarum* on Reducing Cholesterol

In the embodiment of the present invention, in order to test the effect of the *Lactobacillus plantarum* TCI507 on reducing cholesterol, an experiment for reducing the amount of cholesterol in vitro was carried out in a test tube. First, 1% of the strain of the *Lactobacillus plantarum* TCI507 was cultured in a test tube containing MRP (de Man, Rogosa and Sharpe, BD Difco™ Lactobacilli MRS Broth, DF0881175) with 5000 ppm of cholesterol. After incubating at 37° C. for 24 hours, the bacterial solution was centrifuged at 5000 rpm for 10 minutes, and then 5 mL of the supernatant was collected and used the Cholesterol Quantitation Kit (Sigma-Aldrich, USA, MAK043) to quantify the total cholesterol. Wherein, MRS was used as the blank control group; the two strains of *Lactobacillus plantarum* LP1 and LP2, which were isolated by applicant and are test to have the effect of reducing cholesterol, were used as the positive control groups; and the culture solution was prepared by dissolving 55 g of MRS in 1 L of pure water and then sterilizing at 121° C. for 15 minutes.

Figure 1:
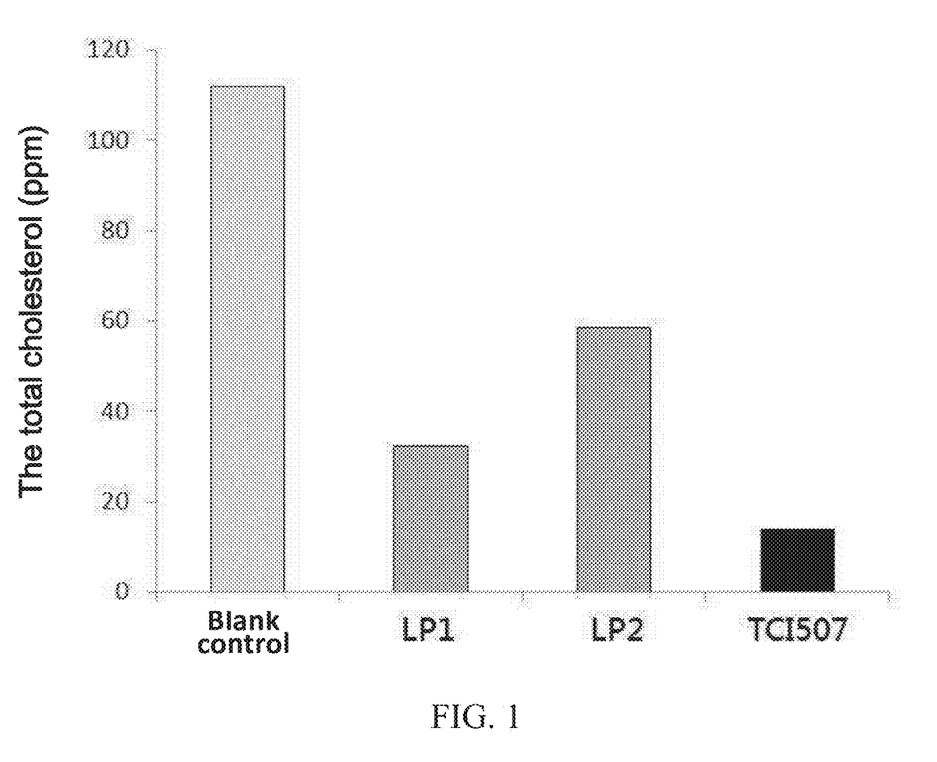
FIG. 1 shows a bar graph that the *Lactobacillus plantarum* TCI507 of the present invention reduces the amount of the total cholesterol.

The results of the *Lactobacillus plantarum* TCI507 of the present invention reduces the amount of the total cholesterol are shown in FIG. 1. As showing in FIG. 1, after the treatment of the *Lactobacillus plantarum* TCI507 of the present invention, the amount of total cholesterol of 87% can be greatly reduced, and the proportion of reduced cholesterol was higher than that of the LP1 (63%) and LP2 (45%) control groups. The result indicates that the *Lactobacillus plantarum* TCI507 of the present invention can effectively reduce the amount of total cholesterol and can be used for cardiovascular healthcare of reducing the cholesterol in the bodies, and not all *Lactobacillus plantarum* show the same high effect of reducing the amount of total cholesterol.

Example 2

Effect of the *Lactobacillus plantarum* on Enhancing the Gene Expression Level of SCARB1, APOA1, and LDLR In the embodiment of the present invention, in order to investigate the *Lactobacillus plantarum* TCI507 on controlling the expression level of cholesterol metabolism-related genes, the human liver epithelial cells, HepG2 cells, which were purchased from the American Type Culture Collection (ATCC) and the number is ATCC® HB-8065™, were used. Wherein, HepG2 cells was cultured in DMEM (Dulbecco's Modified Eagle Medium, Gibco, USA, 12100-046) containing 10% fetal calf serum (Gibco, USA), 1% penicillin-streptomycin (Gibco, USA).

First, $0.5 \times 10^5$ HepG2 cells were cultured in each well of a 6-well culture plate, and cultured at 37° C. for 16 hours, and then the cells were divided into the following five groups: (1) the blank control group only added the cell culture medium, (2) the blank control group only added the bacterial culture medium (i.e. empty culture medium), (3) the positive control group added 1% LP1 metabolite, (4) the positive control group added 1% LP2 metabolite. (5) the experimental group added 1% of the *Lactobacillus plantarum* TCI057 metabolite of the present invention, and the cells of these five groups were incubated at 37° C. for 24 hours, and the expression level of the cholesterol metabolism-related genes in each group of HepG2 cells was measured; wherein 1% the *Lactobacillus plantarum* TCI507, 1% LP1 and 1% LP2 were pre-cultured in MRS at 37° C. for 16 hours (containing about $3 \times 10^9$ cfu/mL) respectively, and then each bacterial solution was centrifuged at 13,000 rpm for 5 minutes to obtain the supernatant, and each of the supernatants was the *Lactobacillus plantarum* TCI507 metabolite, the LP1 metabolite or the LP2 metabolite respectively. HepG2 cells were lysis with cell lysates (Geanaid, Taiwan, RBD300), and then the total RNAs of HepG2 cells were collected from the each of the five groups by the RNA extraction kit (Geneaid, Taiwan, RBD300). Then, 2000 ng of extracted RNAs was subjected to reverse transcription into the target cDNA products with SuperScript® III reverse transcriptase (Invitrogene, USA, No. 18080-051) and the primers in table 1. Then, the cDNA products were used as template and mixed with the target gene primers in table 1 and the mRNA expression level of SCARB1, APOA1, and LDLR of each group were quantified by quantitative real-time polymerase chain reaction (qPCR) with ABI StepOnePlus™ Real-Time PCR System (Thermo Fisher Scientific, USA) and KAPA SYBR FAST (Sigma, USA, No. 38220000000), wherein the PCR conditions were performed as described below: initial step of pre-incubation at 95° C. for 1 min, followed by 40 PCR cycles of 95° C. for 15 secs, 58° C. for 15 secs, 72° C. for 30 secs and then one melting curve cycle. Wherein the quantitative value was taken from the cycle threshold (Ct), and the relative amount of mRNA of the target gene was derived from Equation $2^{-\Delta Ct}$, wherein $\Delta Ct = C_{target\ gene} - Ct_{ACTB}$ (β-actin). The statistically significant difference was determined by the unpaired one-tailed student's t-test of Excel software (*p<0.05;  p<0.01; * p<0.001).

TABLE 1

The sequence of the PCR primer

| Gene | Primer | Number | Primer length (ntds) | Product length (ntds) |
|---|---|---|---|---|
| SCARB1 | SCARB1-F | SEQ ID NO: 1 | 21 | 200 |
|  | SCARB1-R | SEQ ID NO: 2 | 18 |  |
| APOA1 | APOA1-F | SEQ ID NO: 3 | 23 | 200 |
|  | APOA1-R | SEQ ID NO: 4 | 21 |  |
| LDLR | LDLR-F | SEQ ID NO: 5 | 22 | 200 |
|  | LDLR-R | SEQ ID NO: 6 | 23 |  |
| ABCA1 | ABCA1-F | SEQ ID NO: 7 | 23 | 203 |
|  | ABCA1-R | SEQ ID NO: 8 | 24 |  |
| CETP | CETP-F | SEQ ID NO: 9 | 20 | 200 |
|  | CETP-R | SEQ ID NO: 10 | 18 |  |
| β-actin | β-actin-F | SEQ ID NO: 11 | 21 | 250 |
|  | β-actin-R | SEQ ID NO: 12 | 21 |  |

The Scavenger receptor class B member 1 (SCARB1) gene encodes the protein Scavenger receptor class B type 1 (SRB1) which is a membrane receptor of high-density lipoprotein (HDL) cells. High-density lipoprotein collects cholesterol from the blood and deposits the cholesterol in the liver for eventual metabolism. In the process, SRB1 plays a key role. Therefore, the increase expression level of SCARB1 is associated with the decrease of blood cholesterol.

The Apolipoprotein A1 gene (APOA-1) encodes the protein APOA1 which is a major protein component of high-density lipoprotein in the blood, and after being hydrolyzed, it performs the function of promoting the excretion of cholesterol from the tissue to the liver and then the cholesterol would be excreted. APOA1 attaches to the cell membrane and promotes relocation of cholesterol and phospholipids from the inside to the outside of the cell and binding therewith to form HDL. APOA-1 also triggers cholesterol esterification, which converts cholesterol into a form that can be fully integrated into HDL and transported through the blood.

The ATP binding cassette subfamily A member 1 gene (ABCA1) encodes the protein ABCA1 which functions to transport cholesterol from the cell to the extracellular region and is a receptor of APOA-1. Therefore, the increase gene expression level of APOA1 and ABCA1 is associated with the decrease of blood cholesterol.

The low-density lipoprotein receptor gene (LDLR) encodes protein LDLR which is a receptor of the low-density lipoprotein (LDL), wherein LDLR is located on the surface of different types of cells, and would bind with low-density lipoprotein in the blood and then transport the low-density lipoprotein into cells. After the low-density lipoproteins enter into the cell, they would be broken down and release cholesterol. LDLR plays a key role in regulating blood cholesterol levels, and LDLRs are particularly abundant in liver cells, wherein the liver is the organ responsible for removing excess cholesterol from the body. The amount of LDLR on the surface of liver cells determines the rate which cholesterol is removed from the blood. Therefore, the increase gene expression level of LDLR is associated with the decrease of blood cholesterol.

The cholesteryl ester transfer protein gene (CETP) encodes protein CETP which is a plasma protein, and the main function of it is to help transfer cholesterol from high-density lipoprotein to low-density lipoprotein, and the mutation of this gene would lead to high-density lipoproteinemia and arterial atherosclerosis. Therefore, the increase gene expression level of CETP is associated with the decrease of blood cholesterol.

Figure 2:
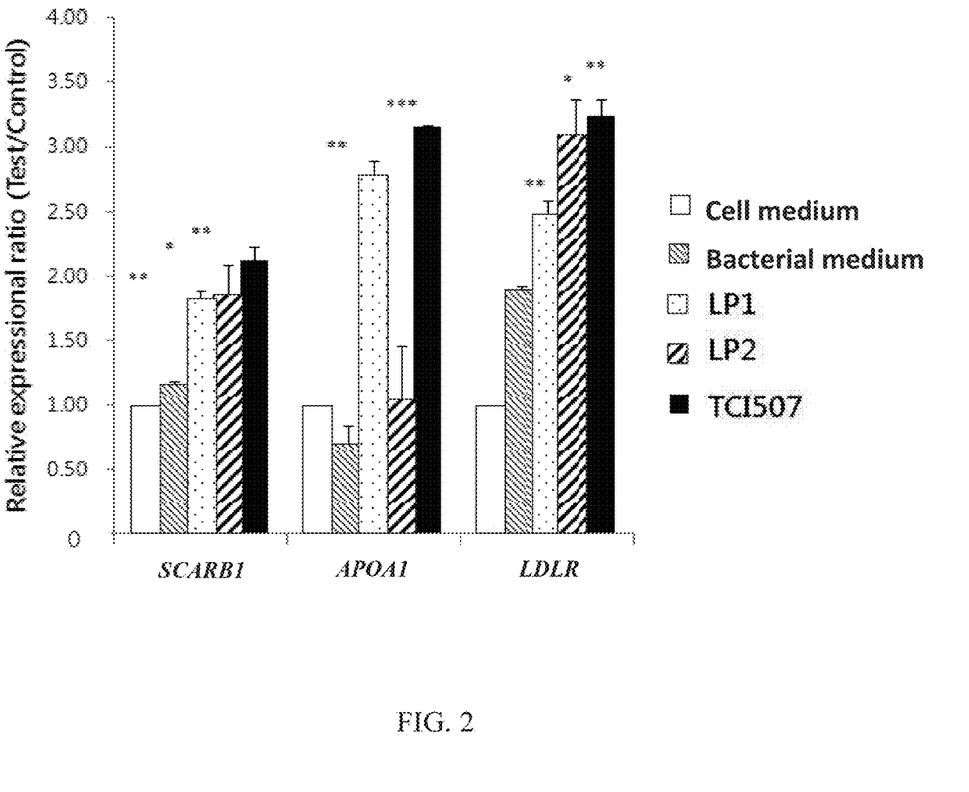
FIG. 2 shows a bar graph that the *Lactobacillus plantarum* TCI507 of the present invention enhances the gene expression level of SCARB1, APOA1, and LDLR. * $p<0.05$;  $p<0.01$; * $p<0.001$.

The results of the *Lactobacillus plantarum* TCI507 of the present invention enhance the gene expression level of SCARB1, APOA1, and LDLR are shown in FIG. 2. As showing in FIG. 2, compared with the blank control group of empty culture medium, the gene expression level of SCARB1 (2 fold to the blank control group), APOA1 (3 fold to the blank control group), and LDLR (3.2 fold to the blank control group) significantly increased after treated with the *Lactobacillus plantarum* TCI507 of the present invention, and the gene expression level of these three genes were all more higher than the positive control groups of LP1 (1.7, 2.4, and 2.8 fold to the blank control group respectively) and LP2 (1.7, 1, and 2.8 fold to the blank control group respectively), which are known with the effect of reducing cholesterol; while the gene expression level of CETP and ABCA1 was not significantly different. The results indicate that the *Lactobacillus plantarum* TCI507 of the present invention can effectively enhance the gene expression level of SCARB1, APOA1, and LDLR and can promote the metabolism of cholesterol and then to be used for cardiovascular healthcare of reducing the cholesterol in the bodies, and not all *Lactobacillus plantarum* show the same high effect of enhancing the gene expression level of SCARB1, APOA1, and LDLR.

Example 3

Effect of the *Lactobacillus Plantarum* TCI507 on Reducing Low-Density Lipoproteins in the Bodies In the embodiment of the present invention, in order to investigate the *Lactobacillus plantarum* TCI507 on reducing low-density lipoproteins in the bodies, 6 subjects were recruited to take a daily dose of $5 \times 10^9$ CFU/cap of the capsules of the *Lactobacillus plantarum* TCI507 of the present invention, and the amount of total cholesterol and the low-density lipoprotein in the blood of the 6 subjects were measured at the time points of before taking, two weeks after taking, and four weeks after taking, respectively; wherein, the changes of the amount of total cholesterol and the low-density lipoprotein in the blood samples of the 6 subjects was administered to the inspection unit.

Figure 3:
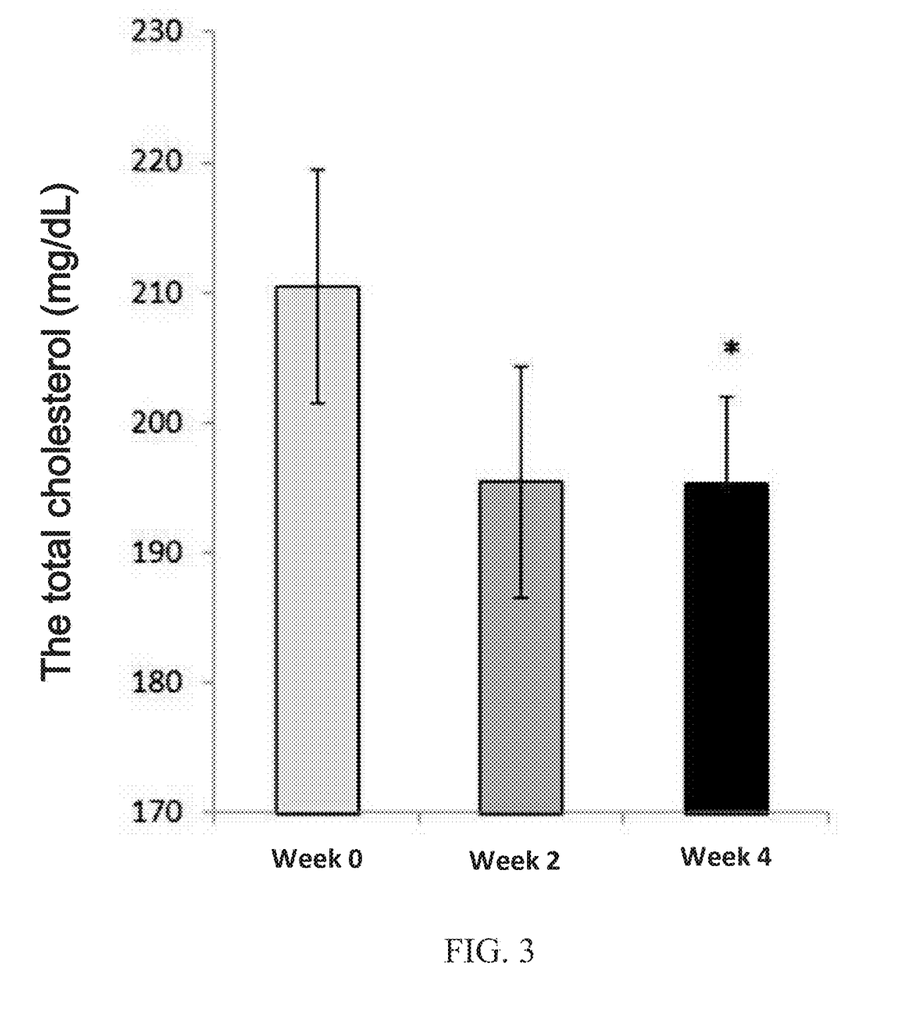
FIG. 3 shows a bar graph that the *Lactobacillus plantarum* TCI507 of the present invention reduces the amount of the total cholesterol in blood. * $p<0.05$.
Figure 4:
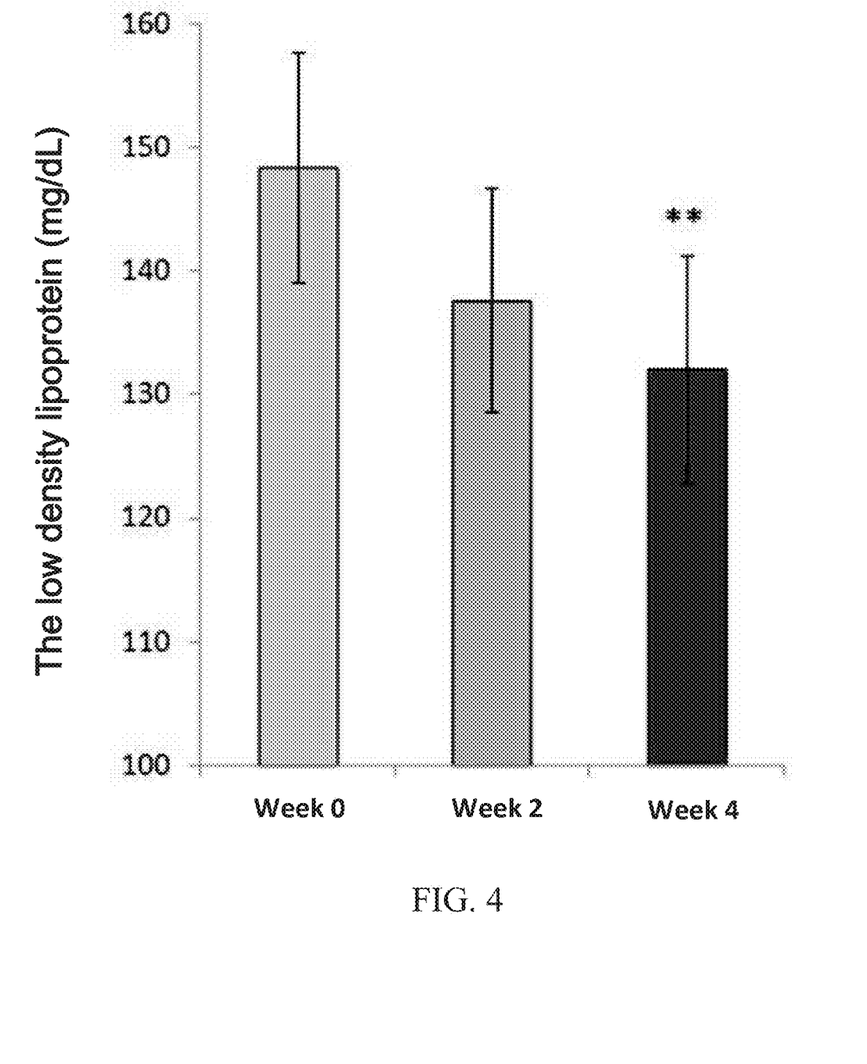
FIG. 4 shows a bar graph that the *Lactobacillus plantarum* TCI507 of the present invention reduces the amount of the low-density lipoprotein in a blood. ** $p<-0.01$.

The results of the *Lactobacillus plantarum* TCI507 of the present invention reduces the amount of total cholesterol in the blood of the bodies are shown in FIG. 3; and the low-density lipoproteins in the blood of the bodies are shown in FIG. 4. As showing in FIG. 3 and FIG. 4, the amount of total cholesterol in the blood of the subjects before taking the *Lactobacillus plantarum* TCI507 of the present invention were about 210 mg/dL, and the low-density lipoprotein content is about 148 mg/dL. After taking the *Lactobacillus plantarum* TCI507 of the present invention for two weeks, the amount of total cholesterol in the blood of the subjects reduced to about 195 mg/dL, and the low-density lipoprotein reduced to about 137 mg/dL. After taking the *Lactobacillus plantarum* TCI507 of the present invention for four weeks, the amount of total cholesterol in the blood of the subjects reduced to about 194 mg/dL, which was 7.2% lower than it before taking, and the low-density lipoprotein reduced to about 131 mg/dL, which was 11% lower than it before taking. The results indicate that the *Lactobacillus plantarum* TCI507 of the present invention can effectively reduce the amount of total cholesterol and low-density lipoprotein in blood, and can be used for cardiovascular healthcare of reducing the cholesterol in the bodies.

In summary, the live bacterium, the deactivated bacterium or the metabolite of the *Lactobacillus plantarum* TCI507 of the present invention can effectively reduce the amount of the cholesterol in vitro showing that they have the potential of lowering cholesterol in bodies; and in cell experiments, the *Lactobacillus plantarum* TCI507 or the metabolite thereof can effectively increase the gene expression level of SCARB1, APOA1, and LDLR, indicating that they can promote the metabolism of cholesterol in bodies; and in vivo, the *Lactobacillus plantarum* TCI507 or the metabolite thereof can further effectively reduce the amount of the total cholesterol and the low-density lipoprotein in blood, showing that they can be used for lowering cholesterol in bodies; and the high cholesterol in blood would cause cardiovascular diseases such as hypertension, arteriosclerosis and myocardial infarction, so the *Lactobacillus plantarum* TCI507 or the metabolite thereof of the present invention can be used for cardiovascular healthcare. Therefore, the *Lactobacillus plantarum* TCI507 or the metabolite thereof of the present invention can be used for the preparation of a cardiovascular healthcare composition for reducing cholesterol, which is a food, a drink, a nutritional supplement, or a pharmaceutical product, and the composition is in a form of a powder, a granule, a solution, a gel can be administered to a subject in need by oral administration or the like.

What is claimed is:

1. A method of reducing cholesterol, comprising administering a composition comprising $5 \times 10^9$ CFUs/individual per day of *Lactobacillus plantarum* TCI507 or a metabolite thereof to a subject in need thereof.

2. The method according to claim 1, wherein the *Lactobacillus plantarum* TCI507 is a live or deactivated bacterium.

3. The method according to claim 1, wherein the concentration of the *Lactobacillus plantarum* TCI507 or the metabolite in the composition is at least 0.5% (w/w).

4. The method according to claim 1, wherein the *Lactobacillus plantarum* TCI507 or the metabolite thereof enhance the gene expression level of Scavenger receptor class B member 1 (SCARB1), Apolipoprotein A1 (APOA1), or Low-density lipoprotein receptor (LDLR).

5. The method according to claim 1, wherein the *Lactobacillus plantarum* TCI507 or the metabolite thereof reduce the level of total cholesterol or low-density lipoprotein (LDL) in the blood.

6. A cholesterol reducing composition, comprising $5\times10^9$ CFUs of *Lactobacillus plantarum* TCI507 and a metabolite thereof, wherein the composition is in the form of a powder, a granule, a solution, or a gel.

7. The composition according to claim 6, wherein the composition is selected from the group consisting of a food, a drink, a nutritional supplement, and a pharmaceutical product.

8. The composition according to claim 6, wherein the composition is for cardiovascular healthcare.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: Artificial sequence
<220> FEATURE:
<223> OTHER INFORMATION: PCR primer

<400> SEQUENCE: 1
actccgactc tgggctcttc a        21

<210> SEQ ID NO 2
<211> LENGTH: 18
<212> TYPE: DNA
<213> ORGANISM: Artificial sequence
<220> FEATURE:
<223> OTHER INFORMATION: PCR primer

<400> SEQUENCE: 2
ggcctccggg ctgtagaa        18

<210> SEQ ID NO 3
<211> LENGTH: 23
<212> TYPE: DNA
<213> ORGANISM: Artificial sequence
<220> FEATURE:
<223> OTHER INFORMATION: PCR primer

<400> SEQUENCE: 3
ctgtgtacgt ggatgtgctc aaa        23

<210> SEQ ID NO 4
<211> LENGTH: 21
<212> TYPE: DNA
<213> ORGANISM: Artificial sequence
<220> FEATURE:
<223> OTHER INFORMATION: PCR primer

<400> SEQUENCE: 4
caggccctct gtctcctttt c        21

<210> SEQ ID NO 5
<211> LENGTH: 22
<212> TYPE: DNA
<213> ORGANISM: Artificial sequence
<220> FEATURE:
<223> OTHER INFORMATION: PCR primer

<400> SEQUENCE: 5
ttcactccat ctcaagcatc ga        22

<210> SEQ ID NO 6
<211> LENGTH: 23
<212> TYPE: DNA
<213> ORGANISM: Artificial sequence
<220> FEATURE:
<223> OTHER INFORMATION: PCR primer

<400> SEQUENCE: 6
ggacagtagg ttttcagcca aca        23

<210> SEQ ID NO 7
<211> LENGTH: 23
<212> TYPE: DNA
<213> ORGANISM: Artificial sequence

```
<220> FEATURE:
<223> OTHER INFORMATION: PCR primer

<400> SEQUENCE: 7
aatcatggtc aatggaaggt tca                                       23

<210> SEQ ID NO 8
<211> LENGTH: 24
<212> TYPE: DNA
<213> ORGANISM: Artificial sequence
<220> FEATURE:
<223> OTHER INFORMATION: PCR primer

<400> SEQUENCE: 8
aagatggaag ctggtattgt agca                                      24

<210> SEQ ID NO 9
<211> LENGTH: 20
<212> TYPE: DNA
<213> ORGANISM: Artificial sequence
<220> FEATURE:
<223> OTHER INFORMATION: PCR primer

<400> SEQUENCE: 9
gcccagacca gcaacattct                                           20

<210> SEQ ID NO 10
<211> LENGTH: 18
<212> TYPE: DNA
<213> ORGANISM: Artificial sequence
<220> FEATURE:
<223> OTHER INFORMATION: PCR primer

<400> SEQUENCE: 10
gatgcccaca gcggtgat                                             18

<210> SEQ ID NO 11
<211> LENGTH: 21
<212> TYPE: DNA
<213> ORGANISM: Artificial sequence
<220> FEATURE:
<223> OTHER INFORMATION: PCR primer

<400> SEQUENCE: 11
catgtacgtt gctatccagg c                                         21

<210> SEQ ID NO 12
<211> LENGTH: 21
<212> TYPE: DNA
<213> ORGANISM: Artificial sequence
<220> FEATURE:
<223> OTHER INFORMATION: PCR primer

<400> SEQUENCE: 12
ctccttaatg tcacgcacga t                                         21
```